United States Patent [19]

Chervu et al.

[11] Patent Number: 4,883,862

[45] Date of Patent: Nov. 28, 1989

[54] MERCAPTOSUCCINYL GLYCYL-GLYCYL-GLYCINE A COMPLEX THEREOF WITH TC-99M, AND METHODS OF MAKING THE SAME

[75] Inventors: Lakshman R. Chervu, Larchmont; Kuldeep K. Bhargava, Bronx; M. Donald Blaufox, Rye, all of N.Y.

[73] Assignee: Albert Einstein College of Medicine - of Yeshiva University, Bronx, N.Y.

[21] Appl. No.: 181,227

[22] Filed: Apr. 13, 1988

[51] Int. Cl.$^4$ .................... H61K 37/02; C07K 5/08
[52] U.S. Cl. .................................. 530/331; 424/1.1; 514/18
[58] Field of Search .................... 530/331; 424/1.1; 514/18

[56] References Cited

U.S. PATENT DOCUMENTS

| | | | |
|---|---|---|---|
| 2,900,375 | 8/1959 | Amiard et al. | 530/331 |
| 4,115,374 | 9/1978 | Ryan et al. | 530/331 |
| 4,382,081 | 5/1983 | Sundeen et al. | 530/331 |
| 4,709,013 | 11/1987 | Nagano | 530/331 |

*Primary Examiner*—Lester L. Lee
*Attorney, Agent, or Firm*—Amster, Rothstein & Ebenstein

[57] ABSTRACT

The novel compound mercaptosuccinyl glycyl-glycyl-glycine (MSG$_3$) and a stable complex thereof with technetium-99m (Tc-99m) having utility as a renal agent. MSG$_3$ is made by coupling glycyl-glycyl-glycine with S-acetyl-mercapto succinic anhydride.

17 Claims, No Drawings

MERCAPTOSUCCINYL GLYCYL-GLYCYL-GLYCINE A COMPLEX THEREOF WITH TC-99M, AND METHODS OF MAKING THE SAME

BACKGROUND OF THE INVENTION

The invention relates to radiolabeled renal agents and more particularly to a technetium-99m-labeled renal agent.

Radionuclidic techniques may provide assessment of glomerular filtration rate (GFR), effective renal plasma flow (ERPF), or individual renal functions. Several agents are currently available for determination of these diagnostic parameters, however, the formulation of a technetium-99m-labeled agent for such determinations has heretofore not been totally satisfactory.

The current tracer of choice for the clinical evaluation of renal tubular function is o-[$^{131}$I]iodohippurate (OIH). Unfortunately, it has the disadvantage of imparting a relatively high absorbed radiation dose to the patient at low diagnostic doses and thus presents a health risk. The radiation dose at 3 hrs after intravenous administration of 500 uCi of I-131 OIH is 47 mrad to a normal kidney and 1.7 rad to the bladder wall. Renal absorbed doses of 3 rad or higher may be encountered in patients with impaired renal function. Although I-123-labeled OIH lowers the radiation dose, it is not available at a reasonable cost for routine use. In addition, the presence of varying amounts of free radioiodine in OIH preparations often poses problems for accurate quantifiable assessment of function.

Technetium-99m (Tc-99m) has ideal physical properties for many applications in nuclear medicine, by virtue of its short half-life and favorable radiation characteristics. The low radiation dose permits the administration of large amounts of activity within short time intervals for serial measurements. Several Tc-99m agents have been reported for use in renal imaging and perfusion studies. Tc-99m diethylenetriaminepentaacetic acid (DTPA) is widely used in clinical nuclear medicine for GFR measurements. Ethylenediaminetetraacetic acid (EDTA) or DTPA complexes of Tc-99m are excreted solely through the slower process of glomerular filtration, and their slow rate of excretion, relative to that of compounds that are actively excreted, is a serious disadvantage. Tc-99m-labeled agents that are cleared rapidly by active tubular excretion, with minimal or preferably no reabsorption from the tubular lumen, would provide significant advantages over the agents mentioned above. They would be excreted within a short time interval, yielding a high target-to-background ratio and minimal radiation dose.

A new class of chelating agents, Tc-99m-DADS [N,N'-bis(mercaptoacetamido)ethylene diamine and its propionic acid derivative], has been reported to have rapid renal excretion consistent with tubular excretion. The renal excretion of DADS is greater than that of Tc-99m DTPA, but lower than that of OIH in rodents. DADS is inferior to OIH in terms of specificity and rate of excretion in normals, and especially in patients with elevated levels of creatinine. The significant biliary excretion of DADS in rats and humans represents a major limitation to its use.

Another class of chelating agents, mercaptoacetyl glycyl-glycyl-glycine (MAG$_3$) based on a triamide monomercaptide tetradentate set of donor groups, is reported to yield a Tc-99m complex which has renal clearance similar to OIH and comparable performance in animal and human studies. However, purification of the Tc-99m-MAG$_3$ complex by high performance liquid chromatography (HPLC) is required prior to its clinical use. The complicated preparatory procedure for these agents, requiring heating and a HPLC purification step to separate the component that shows optimal renal excretion kinetics, precludes their use in a routine clinical setting.

Accordingly, it is an object of the present invention to provide a novel compound and a method of making the same.

It is also an object of the present invention to provide an improved Tc-99m labeled renal agent which overcomes the serious disadvantages inherent in renal agents presently available.

Another object of the present invention is to provide an improved Tc-99m labeled renal agent which is excreted within a relatively short time interval and which yields a high target-to-background ratio with minimal radiation dose.

A further object of the present invention is to provide an improved Tc-99m labeled renal agent which does not require a complicated mode of preparation and therefore may be used in a routine clinical setting.

An additional object of the present invention is to provide a Tc-99m labeled renal agent which is stable.

It is also an object to provide a Tc-99m labeled renal agent which is less of a health risk to the patient from radioactivity than OIH and provides a better target-to-background ratio than Tc-99m labeled MAG$_3$.

SUMMARY OF THE INVENTION

The above and related objects of the present invention are attained in one or another of the various aspects of the present invention.

A first aspect of the present invention is the novel compound mercaptosuccinyl glycyl-glycyl-glycine, hereinafter "MSG$_3$". The compound is preferably capable of forming a stable complex with technetium-99m, hereinafter Tc-99m.

Another aspect of the present invention is a compound comprising a stable complex of Tc-99m and MSG$_3$.

A further aspect of the present invention is a method of forming a compound capable of forming a stable complex with Tc-99m comprising coupling glycyl-glycyl-glycine with S-acetyl-mercapto succinic anhydride.

Yet another aspect of the present invention comprises a method of forming a radiolabeled compound comprising the steps of coupling glycyl-glycyl-glycine with S-acetyl-mercapto succinic anhydride, and forming a stable complex of the product and Tc-99m.

The aforementioned compounds containing Tc-99m are preferably renal agents.

DETAILED DESCRIPTION OF THE PREFERRED EMBODIMENTS

According to the present invention, mercaptosuccinyl glycyl-glycyl-glycine, hereinafter MSG$_3$, is synthesized. Its biological properties render it a replacement for OIH and for mercaptoacetyl glycyl-glycyl-glycine (MAG$_3$) for forming complexes with technetium-99m, hereinafter Tc-99m.

MSG$_3$ is prepared by reacting equimolar amounts of glycyl-glycyl-glycine and S-acetyl-mercapto succinic anhydride in dimethylformamide overnight and crystallization from water, as explained in further detail below under "MSG$_3$ Synthesis." The structure obtained is confirmed by carbon-hydrogen-nitrogen (CHN) analysis and nuclear magnetic resonance (NMR) spectroscopy. The MSG$_3$ is complexed with Tc-99m at room temperature via Sn(II) reduction, as further described below under "Preparation of Tc-99m-MSG$_3$ Complex." The radiochemical purity of the complex is established by both high pressure liquid chromatography (HPLC) and instant thin layer chromatography (ITLC). The biodistribution of the complex Tc-99m-MSG$_3$ is almost identical to that of Tc-99m-MAG$_3$ at all time intervals, except that gastrointestinal elimination of Tc-99m-MAG$_3$ was higher than that of Tc-99m-MSG$_3$, as expounded upon below under "Animal Biodistribution". The rapid secretion of the Tc-99m-MSG$_3$ complex in urine suggest a potential use of MSG$_3$ and its derivatives for complexing with Tc-99m for renal secretory function studies. The ability to use Tc-99m-MSG$_3$ as prepared, without heating and HPLC separation, offers a distinct advantage over the use of Tc-99m-MAG$_3$ in a clinical setting. MSG$_3$ and its derivatives show promise of utility as a chelating agent for proteins in connection with hot labels other than Tc-99m, such as gallium (Ga), indium (In), etc., and with cold labels, such as contrast media, gadiolinium (Gd), iron (Fe), etc., for magnetic resonance imaging (MRI) and other procedures.

MSG$_3$ SYNTHESIS

To a solution of 1.89 g of glycylglycylglycine in 40 ml of DMF solvent at room temperature, an equimolar amount of S-acetyl mercapto succinic anhydride (1.79g) was added and the reaction mixture stirred overnight. DMF was flash evaporated from the reaction mixture and repeated crystallization of the residue from water gave pure product (1.8g) in 47.36% yield according to the following reaction:

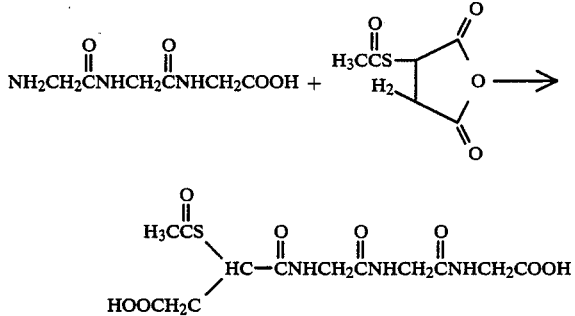

M.P.: 173°-174° C.;
CHN Analysis Calculated for C$_{12}$H$_{17}$O$_8$N$_3$S:
C, 39.63%; H, 4.6%; N, 11.55%;
Found: C, 39.43%; H, 4.68%; N, 11.78%.
NMR(DMSO-d$_6$): 2.32 (3H,S, SCOCH$_3$),
2.60-290 (2H, m, —C—CH2—COO),
3.71 (6H, d, 3 X CH2),
4.31 (1H, t, CH),
8.10 (2H, t, 2X—NH),
8.30 (1H, t, —NH)
12.68 (2H, b,2 X COOH).

PREPARATION OF Tc-99-m-MSG$_3$ COMPLEX 2 mg of the protected ligand was dissolved in 100 ul of 1N NaOH under nitrogen. 40 μg of SnCl$_2$.2H$_2$O in 4N HCl was added, and pH was adjusted to 5.2-5.3 for Sn(II) reduction. Then 2 ml of the complexing agent Tc-99m sodium pertechnetate was added at room temperature. Radiochemical purity of the stable complex was determined by HPLC and ITLC.

A reverse phase HPLC system consisting of a 250×4.1 mm C18 column was run in an isocratic mode at a flow rate of 1 ml/min. An aliquot (25 μl) containing approximately 1 uCi of the preparation of Tc-99m-MSG$_3$ was injected; 0.5 ml fractions were collected and the activity in each fraction determined in a gamma counter. Retention time for the complex was 3.5 min. There was no other radioactivity peak noticed.

Two ITLC solvent systems were developed to determine radiochemical purity: Solvent A, CH$_3$CN/H$_2$O(7:3), and Solvent B, CHCl$_3$/ETOH (3:1). The strips (ITLC-SG) were spotted with 1 ul of the sample and immediately developed for approximately 9 cm, air dried and 1 cm cuts were counted in a well counter to determine the complex, free pertechnetate and reduced-hydrolyzed technetium. The purity of the complex was greater than 95% even after 8 hours.

ANIMAL BIODISTRIBUTION

Initial biodistribution studies were performed in mice (25-30 g) after i.v. injection of a 100 ul volume of the preparation into the tail vein. The animals were killed at different time intervals (six animals for each interval) and the tissues of interest were excised, weighed and their radioactivity counted in a NaI(T1) detector. The % dose/organ was determined by comparison of the tissue radioactivity with suitably diluted aliquots of the injected dose.

The percent administered dose percent at various time intervals post administration (i.e., one hour and two hours) in different organs (i.e. blood, kidney, liver, GI tract) was compared with HPLC purified Tc-99m-MAG$_3$ biodistribution performed in an identical strain of animals. The percent administered dose data (mean +1 SD) of Tc-99m-MSG$_3$ in mice at 120 minutes post injection in blood, GI tract, kidney and liver are 0.5±1.5, 1.5±0.2, 1.8±0.5 and 1.1±0.2, respectively, whereas corresponding values of Tc-99m-MAG$_3$ are 0.3±0.05, 6.6±1.6, 1.1±0.7 and 0.3±0.06, respectively. The data show that the biodistribution of Tc-99m-MSG$_3$ is almost identical to that of Tc-99m-MAG$_3$ at all time intervals, except that gastrointestinal elimination of Tc-99m-MAG$_3$ was higher than that of Tc-99m-MSG$_3$. The lower gastrointestinal elimination of Tc-99m-MSG$_3$ relative to Tc-99m-MAG$_3$ provides a desirably higher target-to-background ratio. The percent administered dose present in the urine at one hour post administration was a desirably high 79.25±5.70.

To summarize, the present invention provides a novel MSG$_3$ compound and an improved Tc-99m labeled renal agent utilizing the same which is stable, overcomes the serious disadvantages inherent in renal agents presently available, and poses a lesser health risk to the patient from radioactivity than OIH. The improved agent is excreted within a relatively short time interval and yields a higher target-to-background ratio with minimal radiation dose than a similar agent utilizing MAG$_3$. Further, it does not require a complicated mode of preparation and may therefore be used in a routine clinical setting.

Now that the preferred embodiments of the present invention have been described in detail, various modifications and improvements thereon will become more readily apparent to those skilled in the art. Accordingly, the appended claims are to be construed broadly in a manner consistent with the spirit and scope of the present invention.

What we claim is:

1. The compound mercaptosuccinyl glycyl-glycyl-glycine.

2. A compound capable of forming a stable complex with technetium-99m comprising mercaptosuccinyl glycyl-glycyl-glycine.

3. The compound of claim 2 characterized by utility as a renal agent.

4. A compound comprising a stable complex of technetium-99m and mercaptosuccinyl glycyl-glycyl-glycine.

5. The compound of claim 4 characterized by utility as a renal agent.

6. A method of forming a compound capable of forming a stable complex with technetium-99m comprising coupling glycyl-glycyl-glycine with S-acetyl-mercapto succinic anhydride.

7. The method of claim 6 wherein said compound is a renal agent.

8. The compound formed by the process of claim 6.

9. A method of forming a radiolabeled compound comprising the steps of:

(A) coupling glycyl-glycyl-glycine with S-acetyl-mercapto succinic anhydride to form a compound, and (B) forming a stable complex of technetium-99m and the compound of step (A).

10. The method of claim 9 wherein said compound is a renal agent.

11. The radiolabeled compound formed by the process of claim 9.

12. The compound of claim 4 wherein said stable complex is formed by the reaction of mercaptosuccinyl glycyl-glycyl-glycine and a pertechnetate at room temperature in the presence of a reducing agent.

13. The compound of claim 12 wherein the stable complex is formed at room temperature.

14. The method of claim 6 wherein said coupling reaction is performed using equimolar amounts of the reactants.

15. The method of claim 14 wherein the coupling reaction is conducted at room temperature.

16. The method of claim 9 wherein the coupling reaction is conducted at room temperature using equimolar amounts of the reactants and the stable complex is formed at room temperature in the presence of a reducing agent.

17. The method of claim 16 wherein the stable complex is formed with the technitium-99m being initially present in the form of a pertechnetate.

* * * * *